United States Patent [19]

Freyne et al.

[11] Patent Number: 5,869,515
[45] Date of Patent: Feb. 9, 1999

[54] 1,3-DIHYDRO-2H-IMIDAZOL-2-ONE COMPOUNDS

[75] Inventors: Eddy Jean Edgard Freyne, Rumst; Gaston Stanislas Marcella Diels, Ravels, both of Belgium; José Ignacio Andrés-Gil, Madrid; Francisco Javier Fernández-Gadea, Toledo, both of Spain

[73] Assignee: Janssen Pharmaceutica N.V., Beerse, Belgium

[21] Appl. No.: 930,478

[22] PCT Filed: Mar. 28, 1996

[86] PCT No.: PCT/EP96/01393

§ 371 Date: Sep. 29, 1997

§ 102(e) Date: Sep. 29, 1997

[87] PCT Pub. No.: WO96/31487

PCT Pub. Date: Oct. 10, 1996

[30] Foreign Application Priority Data

Apr. 6, 1995 [EP] European Pat. Off. .............. 95200870

[51] Int. Cl.$^6$ ...................... A61K 31/415; C07D 233/70; C07D 233/32; C07D 405/04
[52] U.S. Cl. ...................... 514/398; 514/397; 548/324.1; 548/324.5; 548/323.5; 548/311.1
[58] Field of Search .................. 548/324.1; 514/397, 514/398

[56] References Cited

U.S. PATENT DOCUMENTS

| | | | |
|---|---|---|---|
| 4,636,516 | 1/1987 | Kubo et al. | 514/365 |
| 4,845,233 | 7/1989 | Higuchi et al. | 548/324.1 |
| 5,059,237 | 10/1991 | Kohsaka et al. | 548/324.1 X |
| 5,401,851 | 3/1995 | Boyd et al. | 548/112 |

FOREIGN PATENT DOCUMENTS

| | | |
|---|---|---|
| WO 94/02465 | 2/1994 | WIPO . |
| WO 95/04045 | 2/1995 | WIPO . |
| WO 95/20578 | 8/1995 | WIPO . |
| WO 96/00215 | 1/1996 | WIPO . |
| WO 96/00218 | 1/1996 | WIPO . |

OTHER PUBLICATIONS

International Search Report Application Number PCT/EP96/01393 dated Mar.28,1996.

Primary Examiner—Floyd D. Higel

[57] ABSTRACT

The present invention concerns the compounds of formula $$
\begin{array}{c}
R^3 \\
| \\
R^2O - \phantom{X} - C - Alk - N \phantom{X} N - L \\
| \phantom{XXXXXX} \| \phantom{XXXXXXX} / \\
R^1O \phantom{XXXXXXX} X \phantom{XXXX} A - B
\end{array}
\quad (I)
$$

the N-oxide forms, the pharmaceutically acceptable acid or base addition salts and the stereochemically isomeric forms thereof, wherein $R^1$ and $R^2$ each independently are hydrogen; $C_{1-6}$alkyl; difluoromethyl; trifluoromethyl; $C_{3-6}$cycloalkyl; a saturated 5-, 6- or 7-membered heterocycle containing one or two heteroatoms selected from oxygen, sulfur or nitrogen; indanyl; bicyclo[2.2.1]-2-heptenyl; bicyclo[2.2.1]heptanyl; $C_{1-6}$alkylsulfonyl; arylsulfonyl; or substituted $C_{1-10}$alkyl; $R^3$ is hydrogen, halo or $C_{1-6}$alkyloxy $$\diagdown C = X \diagup$$

is a bivalent radical of formula $$\diagdown C = O; \quad \diagdown C = CH - R^4; \quad \diagdown C = N - O - R^5; \text{ or}$$

$$\diagdown C \diagup\negmedspace\negmedspace\negmedspace{(CH_2)_n};$$

Alk is C1-4alkanediyl; —A—B— is a bivalent radical of formula: —CR$^6$═CR$^7$— or —CHR$^6$—CHR$^7$—; L is hydrogen; optionally substituted $C_{1-6}$alkyl; $C_{1-6}$alkylcarbonyl; $C_{1-6}$alkyloxycarbonyl; optionally substituted $C_{3-6}$alkenyl; optionally substituted piperidinyl; $C_{1-6}$alkylsulfonyl or arylsulfonyl; aryl is optionally substituted phenyl; Het$^1$ is morpholinyl or optionally substituted pyridinyl, -furanyl, -thienyl, -hydroxypyridinyl, -imidazolyl, -thiazolyl, -oxazolyl, -isoquinolinyl, -quinolinonyl, -piperidinyl, -piperazinyl; and Het$^2$ is morpholinyl or optionally substituted piperidinyl, -piperazinyl, -pyridinyl, -furanyl or -thienyl; having PDE IV and cytokine inhibiting activity. The invention also relates to processes for preparing the compounds of formula (I) and pharmaceutical compositions thereof.

14 Claims, No Drawings

1,3-DIHYDRO-2H-IMIDAZOL-2-ONE COMPOUNDS

CROSS REFERENCE TO RELATED APPLICATIONS

This application is a 371 of PCT application Ser. No. PCT/EP96/01393, filed Mar. 28, 1996, which claims priority from European Patent Application Serial No. 95.200.870.4, filed on Apr. 6, 1995.

The present invention concerns 1,3-dihydro-2H-imidazol-2-one derivatives having PDE IV and cytokine inhibiting activity and their preparation; it further relates to compositions comprising them, as well as their use as a medicine.

WO 94/12461 generically discloses a number of 1-(benzoylalkyl)-2-hydroxy-imidazole derivatives as selective inhibitors of phosphodiesterase type IV (PDE IV).

Unexpectedly, particular 1,3-dihydro-2H-imidazol-2-one derivatives show improved PDE IV inhibiting activity over the art compounds. In addition, the compounds of the present invention were found to display cytokine inhibiting activity. In view of these pharmacological properties, the present compounds have therapeutical utility in the treatment of disease states related to an abnormal enzymatic or catalytic activity of PDE IV, and/or disease states related to a physiologically detrimental excess of cytokines, in particular allergic, atopic and inflammatory diseases.

The present invention concerns 1,3-dihydro-2H-imidazol-2-one derivatives having the formula

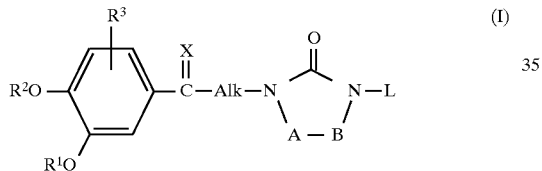

the N-oxide forms, the pharmaceutically acceptable acid or base addition salts and the stereochemically isomeric forms thereof, wherein: $R^1$ and $R^2$ each independently are hydrogen; $C_{1-6}$alkyl; difluoromethyl; trifluoromethyl; $C_{3-6}$cycloalkyl; a saturated 5-, 6- or 7-membered heterocycle containing one or two heteroatoms selected from oxygen, sulfur or nitrogen; indanyl; bicyclo[2.2.1]-2-heptenyl; bicyclo[2.2.1]heptanyl; $C_{1-6}$alkylsulfonyl; arylsulfonyl; or $C_{1-10}$alkyl substituted with one or two substituents each independently selected from aryl, pyridinyl, thienyl, furanyl, $C_{3-7}$cycloalkyl and a saturated 5-, 6- or 7-membered heterocycle containing one or two heteroatoms selected from oxygen, sulfur or nitrogen;

$R^3$ is hydrogen, halo or $C_{1-6}$alkyloxy;

is a bivalent radical of formula

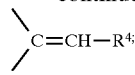

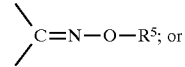

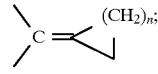

wherein: $R^4$ is hydrogen; cyano; $C_{1-6}$alkyl; $C_{1-4}$alkyloxycarbonyl; $C_{1-6}$alkyl substituted with hydroxy, carboxyl, $C_{1-4}$alkyloxycarbonyl, amino, mono- or di($C_{1-4}$alkyl)amino, $Het^1$ or aryl;

$R^5$ is hydrogen; $C_{1-6}$alkyl; $C_{1-6}$alkyl substituted with hydroxy, carboxyl, $C_{1-4}$alkyloxycarbonyl, amino, aminocarbonyl, mono- or di($C_{1-4}$alkyl)amino, mono- or di($C_{1-4}$alkyl)aminocarbonyl, $Het^1$ or aryl;

n is 1, 2, 3, 4 or 5;

Alk is $C_{1-4}$alkanediyl;

—A—B— is a bivalent radical of formula:

$$-CR^6=CR^7-; \text{ or} \quad (b\text{-}1)$$

$$-CHR^6-CHR^7-; \quad (b\text{-}2)$$

wherein each $R^6$ and $R^7$ independently is hydrogen or $C_{1-4}$alkyl;

L is hydrogen; $C_{1-6}$alkyl; $C_{1-6}$alkylcarbonyl; $C_{1-6}$alkyloxycarbonyl; $C_{1-6}$alkyl substituted with one or two substituents selected from the group consisting of hydroxy, $C_{1-4}$alkyloxy, $C_{1-4}$alkyloxycarbonyl, mono- and di($C_{1-4}$alkyl)amino, aryl and $Het^2$; $C_{3-6}$alkenyl, $C_{3-6}$alkenyl substituted with aryl; piperidinyl: piperidinyl substituted with $C_{1-4}$alkyl or aryl$C_{1-4}$alkyl; $C_{1-6}$alkylsulfonyl or arylsulfonyl;

aryl is phenyl or phenyl substituted with one, two or three substituents selected from halo, hydroxy, $C_{1-4}$alkyl, $C_{1-4}$alkyloxy, $C_{3-6}$cycloalkyl, trifluoromethyl, amino, nitro, carboxyl, $C_{1-4}$alkyloxycarbonyl and $C_{1-4}$alkylcarbonylamino;

$Het^1$ is pyridinyl; pyridinyl substituted with $C_{1-4}$alkyl; furanyl; furanyl substituted with $C_{1-4}$alkyl; thienyl; thienyl substituted with $C_{1-4}$alkylcarbonylamino; hydroxypyridinyl, hydroxypyridinyl substituted with $C_{1-4}$alkyl or $C_{1-4}$alkoxy$C_{1-4}$alkyl; imidazolyl; imidazolyl substituted with $C_{1-4}$alkyl; thiazolyl; thiazolyl substituted with $C_{1-4}$alkyl; oxazolyl; oxazolyl substituted with $C_{1-4}$alkyl; isoquinolinyl; isoquinolinyl substituted with $C_{1-4}$alkyl; quinolinonyl, quinolinonyl substituted with $C_{1-4}$alkyl; morpholinyl; piperidinyl; piperidinyl substituted with $C_{1-4}$alkyl, $C_{1-4}$alkyloxycarbonyl or aryl$C_{1-4}$alkyl; piperazinyl; piperazinyl substituted with $C_{1-4}$alkyl, $C_{1-4}$alkyloxycarbonyl or aryl$C_{1-4}$alkyl; and $Het^2$ is morpholinyl; piperidinyl; piperidinyl substituted with $C_{1-4}$alkyl or aryl$C_{1-4}$alkyl; piperazinyl; piperazinyl substituted with $C_{1-4}$alkyl or aryl$C_{1-4}$alkyl; pyridinyl; pyridinyl substituted with $C_{1-4}$alkyl; furanyl; furanyl substituted with $C_{1-4}$alkyl; thienyl or thienyl substituted with $C_{1-4}$alkyl or $C_{1-4}$alkylcarbonylamino.

Some of the compounds of formula (I) may also exist in their tautomeric forms. Such forms although not explicitly indicated in the above formula are intended to be included within the scope of the present invention.

In $R^1$ and $R^2$, the saturated 5-, 6- or 7-membered heterocycles containing one or two heteroatoms selected from oxygen, sulfur or nitrogen may suitably be selected from heterocycles such as, for example, tetrahydrofuranyl, dioxolanyl, pyrrolidinyl, morpholinyl, piperidinyl, piperazinyl and tetrahydropyranyl. Said heterocyclic radicals are attached to the $C_{1-10}$alkyl radical by any carbon atom or, where appropriate, by a nitrogen atom.

As used in the foregoing definitions the term halo is generic to fluoro, chloro, bromo and iodo; the term $C_{1-4}$alkyl is meant to include straight chained or branched saturated hydrocarbons having from 1 to 4 carbon atoms such as, for example, methyl, ethyl, 1-methylethyl, 1,1-dimethylethyl, propyl, 2-methylpropyl and butyl; the term $C_{1-6}$alkyl is meant to include $C_{1-4}$alkyl and the higher homologues thereof having 5 or 6 carbon atoms such as, for example, 2-methylbutyl, pentyl, hexyl and the like; the term $C_{3-6}$alkenyl defines straight and branch chained hydrocarbon radicals containing one double bond and having from 3 to 6 carbon atoms such as, for example, 2-propenyl, 3-butenyl, 2-butenyl, 2-pentenyl, 3-pentenyl, 3-methyl-2-butenyl and the like; and the carbon atom of said $C_{3-6}$alkenyl being connected to a nitrogen atom preferably is saturated; the term $C_{3-6}$cycloalkyl is generic to cyclopropyl, cyclobutyl, cyclopentyl and cyclohexyl; the term $C_{1-4}$alkanediyl is meant to include straight chained and branched saturated bivalent hydrocarbon radicals having 1 to 4 carbon atoms, such as, for example, methylene, 1,2-ethanediyl, 1,3-propanediyl, 1,4-butanediyl, 2-methyl-1,3-propanediyl and the like.

The pharmaceutically acceptable acid addition salts as mentioned hereinabove are meant to comprise the acid addition salt forms which can conveniently be obtained by treating the base form of the compounds of formula (I) with appropriate acids such as inorganic acids, for example, hydrohalic acid, e.g. hydrochloric or hydrobromic, sulfuric, nitric, phosphoric and the like acids; or organic acids, such as, for example, acetic, hydroxy-acetic, propanoic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely, said acid addition salt forms can be converted in the free base forms by treatment with an appropriate base.

The compounds of formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term addition salt also comprises the hydrates and solvent addition forms which the compounds of formula (I) are able to form. Examples of such forms are e.g. hydrates, alcoholates and the like.

The N-oxide forms of the compounds of formula (I) are meant to comprise those compounds of formula (I) wherein one or several nitrogen atoms are oxidized to the so-called N-oxide.

The term "stereochemically isomeric forms" as used hereinbefore defines all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration. Compounds of formula (I) wherein >C=X is a bivalent radical of formula (a-2) or (a-3), may occur as mixtures of E- and Z-forms, or as pure E-forms or pure Z-forms.

Some of the compounds of formula (I) and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically. The pure and mixed stereochemically isomeric forms of the compounds of formula (I) are intended to be embraced within the scope of the present invention.

An alternative manner of separating the enantiomeric forms of the compounds of formula (I) and intermediates involves liquid chromatography, in particular liquid chromatography using a chiral stationary phase.

Whenever used hereinafter, the term compounds of formula (I) is meant to include also the N-oxide forms, the pharmaceutically acceptable acid or base additions salts and all stereoisomeric forms.

A first set of particular groups of compounds of formula (I) consists of those wherein one or more of the following provisions apply:
  a) $R^1$ is $C_{1-6}$alkyl or $C_{3-6}$cycloalkyl and $R^2$ is $C_{1-6}$alkyl;
  b) $R^3$ is hydrogen;
  c) Alk is methylene or 1,2-ethanediyl;
  d) L is hydrogen or $C_{1-6}$alkyl, preferably L is hydrogen;
  e) —A—B— is a bivalent radical of formula (b-1), preferably a bivalent radical of formula (b-1) wherein $R^6$ and $R^7$ are both hydrogen.

A second set of particular groups of compounds of formula (I) consists of those wherein one or more of the following provisions apply:
  1) $R^1$ is hydrogen; a saturated 5-, 6- or 7-membered heterocycle containing one or two heteroatoms selected from oxygen, sulfur or nitrogen; bicyclo[2.2.1]-2-heptenyl; $C_{1-6}$alkylsulfonyl; arylsulfonyl; or $C_{1-10}$alkyl substituted with one or two substituents each independently selected from pyridinyl, thienyl, furanyl, $C_{3-7}$cycloalkyl and a saturated 5-, 6- or 7-membered heterocycle containing one or two heteroatoms selected from oxygen, sulfur or nitrogen;
  2) $R^2$ is hydrogen, $C_{3-6}$cycloalkyl; a saturated 5-, 6- or 7-membered heterocycle containing one or two heteroatoms selected from oxygen, sulfur or nitrogen; indanyl; bicyclo[2.2.1]-2-heptenyl; bicyclo[2.2.1] heptanyl; $C_{1-6}$alkylsulfonyl; arylsulfonyl; or $C_{1-10}$alkyl substituted with one or two substituents each independently selected from aryl, pyridinyl, thienyl, furanyl, $C_{3-7}$cycloalkyl and a saturated 5-, 6- or 7-membered heterocycle containing one or two heteroatoms selected from oxygen, sulfur or nitrogen;

3) $R^3$ is halo or $C_{1-6}$alkyloxy;

4)

is a radical of formula (a-2), (a-3) or (a-4);

5) —A—B— is a bivalent radical of formula (a-2);

6) L is $C_{1-6}$alkylcarbonyl; $C_{1-6}$alkyl substituted with hydroxy or $C_{1-4}$alkyloxy; $C_{3-6}$alkenyl; $C_{3-6}$alkenyl substituted with aryl; $C_{1-6}$alkylsulfonyl or arylsulfonyl.

An interesting subgroup within said second set of groups consists of those compounds of formula (I) wherein

is a radical of formula (a-2), (a-3) or (a-4).

Another interesting subgroup within said second set of groups consists of those compounds of formula (I) wherein $R^1$ is hydrogen; a saturated 5-, 6 - or 7-membered heterocycle containing one or two heteroatoms selected from oxygen, sulfur or nitrogen; bicyclo[2.2.1]-2-heptenyl; $C_{1-6}$alkylsulfonyl; arylsulfonyl; or $C_{1-10}$alkyl substituted with one or two substituents each independently selected from pyridinyl, thienyl, furanyl, $C_{3-7}$cycloalkyl and a saturated 5-, 6- or 7-membered heterocycle containing one or two heteroatoms selected from oxygen, sulfur or nitrogen.

Still another interesting subgroup within said second set of groups consists of those compounds of formula (I) wherein $R^2$ is hydrogen, $C_{3-6}$cycloalkyl; a saturated 5-, 6- or 7-membered heterocycle containing one or two heteroatoms selected from oxygen, sulfur or nitrogen; indanyl; bicyclo[2.2.1]-2-heptenyl; bicyclo[2.2.1]heptanyl; $C_{1-6}$alkylsulfonyl; arylsulfonyl; or $C_{1-10}$alkyl substituted with one or two substituents each independently selected from aryl, pyridinyl, thienyl, furanyl, $C_{3-7}$cycloalkyl and a saturated 5-, 6- or 7-membered heterocycle containing one or two heteroatoms selected from oxygen, sulfur or nitrogen.

Preferred compounds are those compounds of formula (I) wherein $R^1$ is $C_{1-6}$alkyl, $C_{3-6}$cycloalkyl or $C_{1-10}$alkyl substituted with $C_{3-7}$cycloalkyl; $R^2$ is $C_{1-6}$alkyl; and

is a bivalent radical of formula (a-1), (a-2) or (a-3).

Most preferred are the compounds 1-[2-[3-(cyclopentyloxy)-4-methoxyphenyl]-2-oxoethyl]-1,3-dihydro-2H-imidazol-2-one; 1-[2-[3-(cyclopentyloxy)-4-methoxy-phenyl]-2-propenyl]-1,3-dihydro-2H-imidazol-2-one; their pharmaceutically acceptable acid or base addition salts and their stereoisomeric forms.

Whenever used hereinafter, $R^1$ to $R^7$,

Alk, —A—B— and L are defined as under formula (I) unless otherwise indicated.

The compounds of formula (I) can generally be prepared by N-alkylating a 1,3-dihydro-2H-imidazol-2-one derivative of formula (II) with an appropriately substituted alkylating agent of formula (III), wherein $W^1$ is a reactive leaving group such as, for example, a halogen.

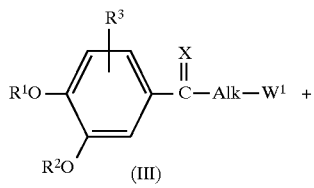

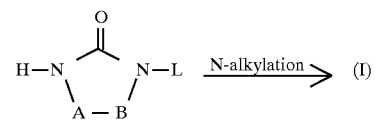

Said N-alkylation may conveniently be performed in the presence of a base such as, for example, sodium hydride, butyllithium or sodium bis(trimethylsilyl)amide, in a reaction-inert solvent such as, for example, tetrahydrofuran, optionally cooled on an ice-bath. The reaction is preferably performed under a reaction inert atmosphere such as, for example, oxygen free nitrogen. It may be advantageous to add to the reaction mixture a crown ether, e.g. 1,4,7,10,13,16-hexaoxacyclooctadecane and the like or a complexing agent such as for example, tris[2-(2-methoxyethoxy)]ethanamine and the like. Stirring may enhance the rate of the reaction. In case intermediates of formula (II), wherein L is replaced by a suitable protecting group, are used in said N-alkylation reaction, compounds of formula (I) wherein L is hydrogen, said compounds being represented by compounds of formula (I-a), may be obtained using art-known deprotection reactions.

In this and the following preparations, the reaction products may be isolated from the reaction medium and, if necessary, further purified according to methodologies generally known in the art such as, for example, extraction, crystallization, trituration and chromatography.

Alternatively, compounds of formula (I) may be prepared by reacting an organometallic intermediate of formula (IV), wherein M is an appropriate metal ion or metalcomplex ion such as, for example, $Li^+$, $(MgBr)^+$, $B(OH)_2^+$ or $Sn(CH_3)_3^+$, with a suitable 1,3-dihydro-2H-imidazol-2-one derivative of formula (V) wherein $W^2$ is a reactive leaving group such as, for example, a halogen or a substituted amine.

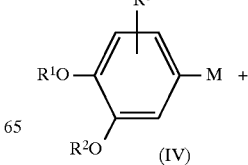

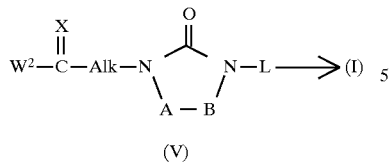

(V)

Said reaction may be performed in a reaction-inert solvent such as, for example, dimethoxyethane, tetrahydrofuran or diethylether. Stirring and heating may enhance the rate of the reaction. In case intermediates of formula (V), wherein L is replaced by a suitable protecting group, are used in said reaction, compounds of formula (I) wherein L is hydrogen, said compounds being represented by compounds of formula (I-a), may be obtained using art-known deprotection reactions.

The compounds of formula (I) can also be converted into each other following art-known procedures of functional group transformation.

In particular, compounds of formula (I) wherein L is other than hydrogen, said compounds being represented by formula (I-b), may be prepared by reacting a compound of formula (I-a) with L'-W$^3$ (VI) wherein L' is the same as L but other than hydrogen, and W$^3$ is a reactive leaving group such as, for example, a halogen atom.

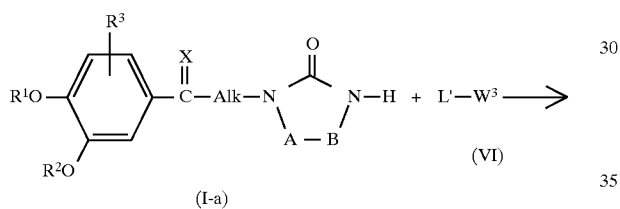

(I-a)  (VI)

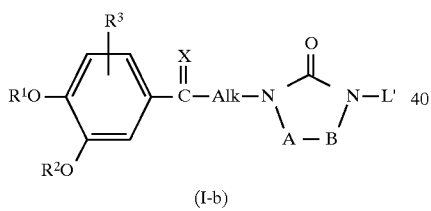

(I-b)

Also art-known addition reactions may be used to convert compounds of formula (I-a) into compounds of formula (I-b).

The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with 3-phenyl-2-(phenylsulfonyl)oxaziridine or with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

Compounds of formula (I) wherein

is a radical of formula (a-1), said compounds being represented by (I-1) may be prepared by oxidation of an intermediate of formula (VII) with a suitable oxidizing agent such as, for example, oxalyl chloride, in the presence of an appropriate base such as, for example, triethylamine, and in a reaction-inert solvent such as, for example, dichloromethane. The reaction is conveniently carried at low temperatures, for instance −60° C., and under an oxygen free atmosphere, for instance, a N$_2$ atmosphere.

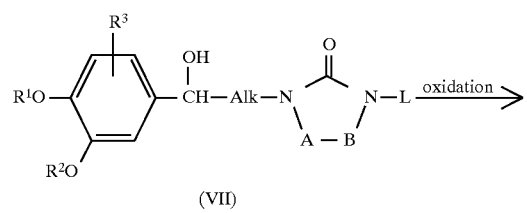

(VII)

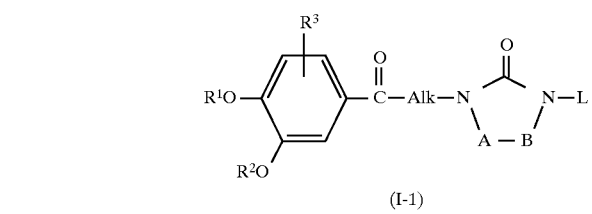

(I-1)

Compounds of formula (I-1) may further be reacted with a Wittig reagent of formula (VIII) wherein Y is a suitable counter ion such as, for example, a halogen, thus forming a compound of formula (I) wherein <C=x is a radical (a-2), said compounds being represented by formula (I-2). Said reaction may be performed in a reaction-inert solvent in the presence of a base such as, for example, butyllithium or sodium hydride. The phosphonium salt-type intermediates of formula (VIII) may conveniently be replaced by the corresponding more reactive phosphonic ester-type intermediates of formula (VIII).

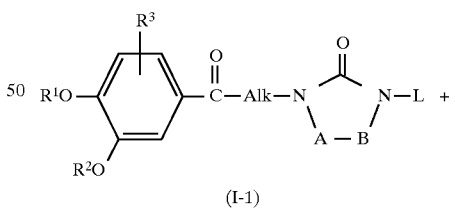

(I-1)

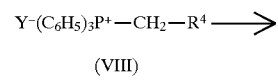

(VIII)

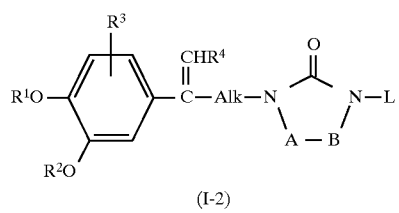

(I-2)

Compounds of formula (I) wherein

is a radical of formula (a-3) and $R^5$ is hydrogen, said compounds being represented by formula (I-3-1), may be prepared by reacting a compound of formula (I-1) with hydroxylamine or a functional derivative thereof, in a reaction-inert solvent such as, for example, ethanol or pyridine, and optionally in the presence of a base such as, for example, sodium carbonate or diethylethanamine. The thus obtained oxime of formula (I-3-1) may be reacted with $R^{5'}$-$W^4$ (IX) wherein $W^4$ is a reactive leaving group such as, for example, a halogen atom, and $R^{5'}$ is the same as $R^5$ but other than hydrogen, thus obtaining a compound of formula (I-3-2).

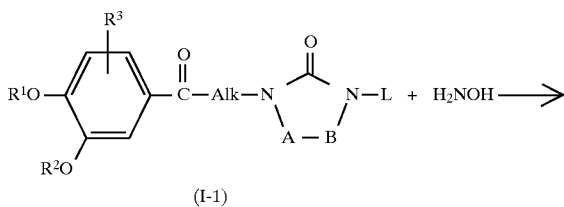

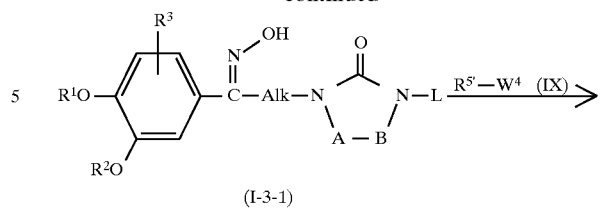

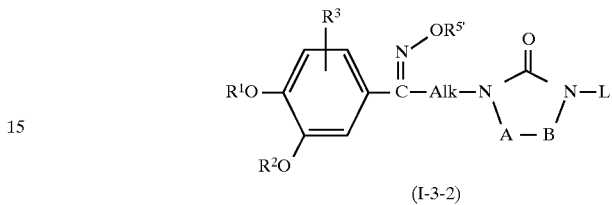

The reagents and intermediates of formula (II), (III), (IV), (V), (VI), (VIII) and (IX) required for the synthesis of the compounds of the present invention are either commercially readily available, or may be prepared according to known procedures.

Intermediates of formula (VII) wherein L is hydrogen and Alk is methylene, said intermediates being represented by formula (VII-a), may be prepared following the reaction process as depicted in scheme 1.

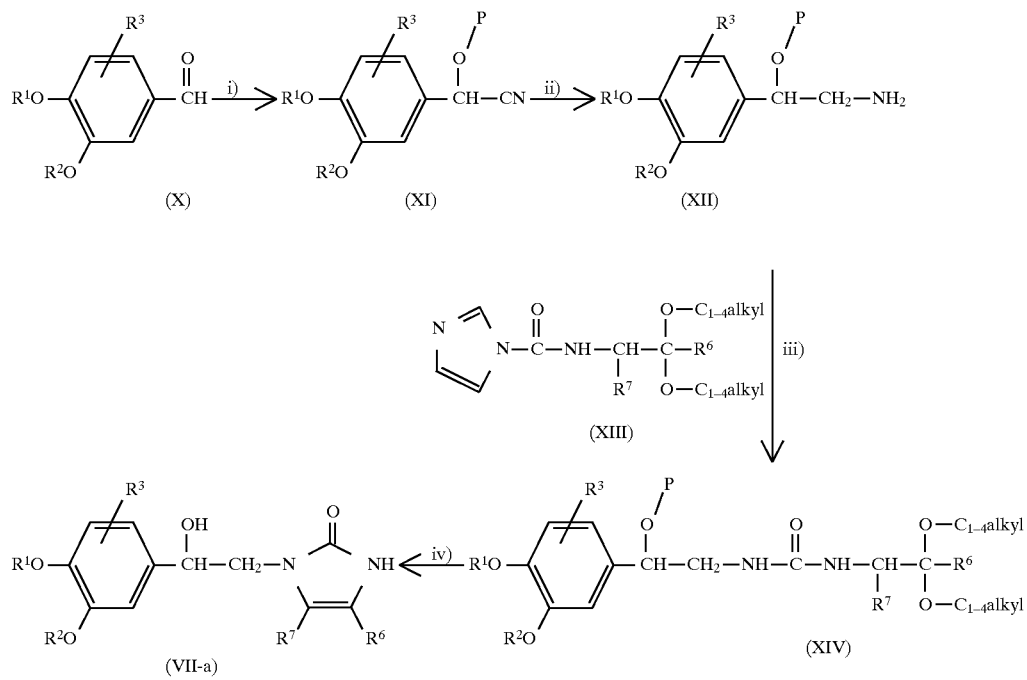

Scheme 1

Step i) in scheme 1 involes the reaction of an intermediate of formula (X) with trimethylsilyl cyanide or a functional derivative thereof in the presence of a suitable catalyst such as, for example, zinc iodide, and in a reaction-inert solvent such as, for example, dichloromethane; thus forming an intermediate of formula (XI) wherein P is a trimethylsilyl protecting group or a functional derivative thereof. Depending on the nature of the $R^1$, $R^2$ and $R^3$ variables, P may also be hydrogen. Subsequently, in step ii), the nitrile derivative of formula (XI) may be reduced to the corresponding amine of formula (XII) using art-known techniques such as, for example, reduction with hydrogen in the presence of a suitable catalyst such as, for example, Raney nickel. Further, in step iii), an intermediate of formula (XII) may be reacted with an imidazole derivative of formula (XIII) in a reaction-inert solvent such as, for example, tetrahydrofuran, preferably a temperature ranging between room temperature and reflux temperature; thus forming an intermediate of formula (XIV). Finally, step iv) involes the cyclization of an intermediate of formula (XIV) to an intermediate of formula (VII-a) in the presence of a suitable acid such as, for example, hydrochloric acid.

The compounds of formula (I), the N-oxide forms, pharmaceutically acceptable acid or base addition salts and the stereochemically isomeric forms thereof, are potent inhibitors of the phosphodiesterase (PDE) isoenzymes of family IV (cAMP-specific family).

cAMP (adenosine cyclic 3',5'-monophosphate) is a key second messenger, the concentration of which affects particular cell activities through activation of enzymes such as kinases. PDE IV is known to hydrolyse cAMP to its corresponding inactive 5'-monophosphate metabolite. Hence, inhibition of PDE IV leads to an elevation of cAMP levels in particular cells such as the respiratory smooth muscle cell and in a wide variety of inflammatory cells, i.e. certain lymphocytes, e.g. basophils, neutrophils and eosinophils, monocytes and mast-cells. A number of allergic, atopic and inflammatory diseases are deemed to be caused by higher-than-normal PDE IV concentrations which result in low cAMP levels and hypersensitivity of the thus affected cells for excitatory stimuli. (Examples of said hypersensitivity are for example, excessive histamine release from basophils and mast cells or excessive superoxide anion radical formation by eosinophils.) Hence, the present compounds having potent phosphodiesterase IV inhibitory properties are deemed useful agents in alleviating and/or curing allergic, atopic and inflammatory diseases. The functional effects of PDE IV inhibitors are e.g. respiratory smooth muscle relaxation, bronchodilation, platelet aggregation inhibition and inhibition of white blood cell mediator release. Examples of allergic diseases are bronchial asthma, cheilitis, conjunctivitis, contact dermatitis and eczema, irritable bowel disease, deshydroform eczema, urticaria, vasculitis, vulvitis; examples of atopic diseases are dermatitis and eczema, winterfeet, asthma, allergic rhinitis; and related afflictions are, for example, psoriasis and other hyperproliferative diseases.

The present invention thus also relates to compounds of formula (I) as defined hereinabove for use as a medicine, in particular for use as an anti-asthmatic medicine or as a medicine for treating atopic diseases. Thus the compounds of the present invention may be used for the manufacture of a medicament for treating asthmatic or atopic diseases, more in particular atopic dermatitis.

The PDE IV inhibitory activity of the compounds of formula (I) may be demonstrated in the test "Inhibition of recombinant human mononuclear lymphocyte (MNL) phosphodiesterase type IV B produced in insect cells with a baculovirus vector". Several in vivo and in vitro tests may be used to demonstrate the usefulness of the compounds of formula (I) in treating the described allergic, atopic and inflammatory diseases. Such tests are for instance, "Bronchoconstriction of the guinea pig trachea in vitro", "Bronchoconstriction of the guinea pig trachea in vivo" and the in vivo test "Dextran-induced oedema formation in mouse ear".

Further, the present compounds have only very low inhibitory activity on the phosphodiesterase isoenzymes of family III (cGMP-inhibited family). Inhibition of, in particular, PDE III leads to an elevation of cAMP in the cardiac muscle, thereby causing effects on the contractile force of the heart as well as on the relaxation of the heart. In the treatment of the described allergic, atopic and inflammatory diseases, cardiovascular effects clearly are undesired. Hence, as the present compounds inhibit PDE IV at much lower concentrations as they inhibit PDE III, their therapeutic use may be adjusted to avoid cardiovascular side-effects.

Art-known PDE IV inhibitors often cause adverse gastro-intestinal side effects. Most of the present compounds, however, have few effects on the gastro-intestinal tract, which may be demonstrated in the test "Gastric emptying of a caloric meal in rats".

The designation PDE III and IV as used herein refers to the classification by J. A. Beavo and D. H. Reifsnyder, TIPS Reviews, April 1990, pp. 150–155.

The compounds of the present invention also have cytokine inhibitory activity. A cytokine is any secreted polypeptide that affects the function of other cells by modulating interactions between cells in the immune or inflammatory response. Examples of cytokines are monokines and lymphokines and they may be produced by a wide variety of cells. For instance, a monokine is generally referred to as being produced and secreted by a mononuclear cell, such as a macrophage and/or monocyte but many other cells produce monokines, such as natural killer cells, fibroblasts, basophils, neutrophils, endothelial cells, brain astrocytes, bone marrow stromal cells, epideral keratinocytes, and β-lymphocytes. Lymphokines are generally referred to as being produced by lymphocyte cells. Examples of cytokines include Interleukin-1 (I-1), Interleukin-2 (IL-2), Interleukin-6 (IL-6), Interleukin-8 (IL-8), alpha-Tumor Necrosis Factor (αTNF) and beta-Tumor Necrosis Factor (βTNF).

The cytokine specifically desired to be inhibited is αTNF. Excessive or unregulated TNF production is implicated in mediating or exacerbating a number of diseases including rheumatoid arthritis, rheumatoid spondylitis, osteoarthritis, gouty arthritis, and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcoidosis, bone resorption diseases, reperfusion injury, graft versus host reaction, allograft rejections, fever and myalgias due to infection, such as influenza, cachexia secondary to infection or malignancy, cachexia secondary to acquired immune deficiency syndrome (AIDS), AIDS, ARC (AIDS related complex), keloid formation, scar tissue formation, Crohn's disease, ulcerative colitis, or pyresis.

The cytokine inhibitory activity of the compounds of formula (I), such as the inhibition of αTNF production, may be demonstrated in the in vitro test "Cytokine production in human whole blood cultures".

In addition, the compounds of the present invention are expected to show no or little endocrinological side-effects. This may be evidenced by, for instance, the "Testosterone in vivo" test, the "In vitro inhibition of the aromatase activity"-test and the "In vivo inhibition of the aromatase activity"-test.

In view of their useful PDE IV and cytokine inhibiting properties, the subject compounds may be formulated into various pharmaceutical forms for administration purposes. To prepare the pharmaceutical compositions of this invention, an effective amount of the particular compound, in base or acid addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for administration orally, rectally, topically, percutaneously, by inhalation or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment. As appropriate compositions for topical application there may be cited all compositions usually employed for topically administering drugs e.g. creams, gellies, dressings, shampoos, tinctures, pastes, ointments, salves, powders and the like. Application of said compositions may be by aerosol, e.g. with a propellent such as nitrogen, carbon dioxide, a freon, or without a propellent such as a pump spray, drops, lotions, or a semisolid such as a thickened composition which can be applied by a swab. In particular, semisolid compositions such as salves, creams, gellies, ointments and the like will conveniently be used.

In order to enhance the solubility and/or the stability of the compounds of formula (I) in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin. Also co-solvents such as alcohols may improve the solubility and/or the stability of the compounds of formula (I) in pharmaceutical compositions. In the preparation of aqueous compositions, addition salts of the subject compounds are obviously more suitable due to their increased water solubility.

It is especially advantageous to formulate the aforementioned pharmaceutical compositions in dosage unit form for ease of administration and uniformity of dosage.

Dosage unit form refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions and the like, and segregated multiples thereof.

The present invention also relates to a method of treating warm-blooded animals suffering from disease states related to an abnormal enzymatic or catalytic activity of PDE IV, and/or disease states related to a physiologically detrimental excess of cytokines, in particular allergic, atopic and inflammatory diseases, more in particular asthmatic and atopic diseases, most particular atopic dermatitis. Said method comprises the administration of a therapeutically effective amount of a compound of formula (I) or a N-oxide form, a pharmaceutically acceptable acid or base addition salt or a stereochemically isomeric form thereof in admixture with a pharmaceutical carrier.

In general it is contemplated that an effective daily amount would be from 0.01 mg/kg to 10 mg/kg body weight, more preferably from 0.04 mg/kg to 5 mg/kg body weight. It is evident that said effective daily amount may be lowered or increased depending on the response of the treated subject and/or depending on the evaluation of the physician prescribing the compounds of the instant invention. The effective daily amount ranges mentioned hereinabove are therefore guidelines only and are not intended to limit the scope or use of the invention to any extent.

The following examples are intended to illustrate and not to limit the scope of the present invention.

EXPERIMENTAL PART

Compounds of formula (I) and some intermediates have a stereogenic center. In those cases where the racemate was separated into its enantiomers, the stereochemically isomeric form which was first isolated was designated as "A" and the second as "B", without further reference to the actual stereochemical configuration.

Hereinafter, "THF" means tetrahydrofuran and "RT" means room temperature.

A. PREPARATION OF THE INTERMEDIATES

EXAMPLE A.1

Under a $N_2$ flow, a solution of benzyltrimethylammonium dichloroiodate (78 g) in THF (250 ml) was added to a mixture of 1-[3-(cyclopentyloxy)-4-methoxyphenyl] ethanone (26.3 g) in THF (250 ml) while stirring. The resulting reaction mixture was stirred for 16 hours at RT. The solvent was evaporated and the residue was redissolved in diethyl ether (300 ml). The mixture was added dropwise to a 5% $Na_2S_2O_4$ solution (400 ml). The aqueous layer was extracted twice with diethyl ether (2×100 ml). The combined organic layers were washed with water (2×500 ml), dried over $MgSO_4$, filtered and the solvent evaporated. The crude oil was crystallized from hexane. The precipitate was filtered off, washed with hexane and dried, yielding 11 g of 2-chloro-1-[3-(cyclopentyloxy)-4-methoxyphenyl]ethanone. The filtrate was evaporated and the residue was crystallized from hexane. The precipitate was filtered off and dried, yielding 7.4 g (24.6%) of 2-chloro-1-[3-(cyclopentyloxy)-4-methoxyphenyl]ethanone (interm. 1).

EXAMPLE A.2 a) A solution of 4-methoxybenzenemethanamine (72.7 g) and triethylamine (83.6 ml) in $CH_2Cl_2$ (750 ml) was cooled on an ice-bath. Phenylchloroformate (91.4 g) was added dropwise and the reaction mixture was stirred at RT. The reaction mixture was washed three times with water and the precipitate was filtered off. The organic layer was separated, washed three times with a 5% aqueous $NaHCO_3$ solution, dried ($MgSO_4$), filtered and the solvent was evaporated. The precipitate was stirred in boiling diethyl ether (300 ml), filtered off and dried, yielding 84.4 g (65.5%) of phenyl [(4-methoxyphenyl)methyl]carbamate (interm. 2).

b) A mixture of 2,2-dimethoxyethylamine (41.5 ml) and N,N-dimethyl-4-pyridinamine (21.2 g) in triethylamine (96.7 ml) was added to a solution of intermediate 2 (84.4 g) in 1,4-dioxane (1000 ml). stirred at RT. The reaction mixture was stirred and refluxed overnight. The solvent was evaporated and the residue was taken up in $CH_2Cl_2$ and washed with 1N NaOH. The organic layer was separated, dried ($MgSO_4$), filtered and the solvent was evaporated. The residue was taken up in $CH_2Cl_2$, washed three times with 1N HCl, washed with a 5% aqueous $NaHCO_3$ solution, dried ($MgSO_4$), filtered, and the solvent was evaporated, yielding 82.3 g of N-(2,2-dimethoxyethyl)-N'-[(4-methoxyphenyl)methyl]urea (interm. 3).

c) A solution of intermediate 3 (19 g) in methanol (572 ml) and water (143 ml) was cooled to 5° C. HCl (224 ml; o.5N) was added dropwise. The mixture was allowed to warm to RT. The reaction mixture was stirred for 4 days at RT and filtered. NaOH (112 ml; 1N) was added slowly to the filtrate, and the solvent was evaporated. The desired product precipitated from the aqueous concentrate. $CH_2Cl_2$ was added to dissolve this compound. The organic layer was separated, washed with water, dried ($MgSO_4$), filtered and the solvent was evaporated. The solid residue was crystallized from ethylacetate. The precipitate was filtered off, washed with ethylacetate and diethyl ether, then dried, yielding 9.8 g (64%) of 1,3-dihydro-1-[(4-methoxyphenyl)methyl]-2H-imidazol-2-one (interm.4; mp. 132.4° C.).

Using a similar procedure 1-[(2,4-dimethoxyphenyl)methyl]-1,3-dihydro-2H-imidazol-2-one was prepared (interm. 5; mp. 160.8° C.).

EXAMPLE A.3

A mixture of (±)-N-[2-[3-(cyclopropylmethoxy)-4-methoxyphenyl]-2-[(trimethylsilyl)-oxy]ethyl]-N-(dimethoxyethyl)urea (39.6 g) and HCl (150 ml) in methanol (450 ml) was stirred for 48 hours at RT. The resulting mixture was concentrated and the concentrate (150 ml) was extracted three times with $CH_2Cl_2$. The combined organic layer were poured out into a NaOH solution. The mixture was stirred and the layers were separated. The aqueous phase was extracted twice with $CH_2Cl_2$. The separated organic layer was dried ($MgSO_4$), filtered, and the solvent was evaporated. The residue was purified by column chromatography over silica gel (eluent: $CH_2Cl_2$/($CH_3OH/NH_3$) 95/5). The pure fractions were collected and the solvent was evaporated. The residue was crystallized from ethylacetate/ diisopropyl ether. The precipitate was filtered off and dried, yielding 10.36 g (37.9%) of 1-[2-[3-(cyclopropylmethyloxy)-4-methoxyphenyl]-2-hydroxyethyl]-1,3-dihydro-2H-imidazol-2-one (interm. 6).

B. PREPARATION OF THE FINAL COMPOUNDS

EXAMPLE B.1 a) Sodium bis(trimethylsilyl)amide (5 ml) was added to a solution of 1,3-dihydro-2H-imidazol-2-one (0.84 g) in N,N-dimethylformamide (50 ml), stirred under a $N_2$ flow and cooled in an ice-bath. The reaction mixture was stirred for 30 minutes. Intermediate 1 (2.69 g) was added portionwise and the resulting reaction mixture was stirred for 16 hours at RT, then for 2 hours at 50° C. The reaction mixture was stirred in methyl isobutyl ketone (200 ml)/(50 ml) water. The solvent was evaporated and methyl isobutyl ketone (100 ml) was added and azeotroped on the rotary evaporator. The mixture was purified by column chromatography over silica gel (eluent: $CH_2Cl_2$/($CH_3OH/NH_3$) 97/3). The desired fractions were collected and the solvent was evaporated. The white solid was stirred in diisopropyl ether, filtered off, washed with diisopropyl ether and dried, yielding 0.4 g (12.6%) of 1-[2-[3-(cyclopentyloxy)-4-methoxyphenyl]-2-oxoethyl]-1,3-dihydro-2H-imidazol-2-one (comp. 1; mp. 201.1° C.).

b) A suspension of compound 1 (3.6 g) in ethyl chloroformate (30 ml) was stirred and refluxed for 1 hour. The solvent was evaporated and the residue was redissolved in toluene. The solvent was evaporated again. The residue was purified by column chromatography over silica gel (eluent: $CH_2Cl_2$/($CH_3OH/NH_3$) 99/1). The pure fractions were collected and the solvent was evaporated under reduced pressure. The residue was treated with ethylacetate and the solvent was evaporated. The residue (1.1 g) was purified by HPLC over silica gel (eluent: $CH_2Cl_2$/$CH_3OH$ 100/0 to 98/2). The pure fractions were collected and the solvent was evaporated under reduced pressure. The residue (0.46 g) was taken up in ethylacetate and the solvent was evaporated under reduced pressure. The residue was triturated in diisopropyl ether. The precipitate was filtered off, washed with diisopropyl ether and dried, yielding 0.4 g (10.3%) ethyl 3-[2-[3-(cyclopentyloxy)-4-methoxphenyl]-2-oxoethyl]-2, 3-dihydro-2-oxo-1H-imidazole-1-carboxylate (comp. 2; mp. 81.3° C.).

c) A mixture of compound 1 (3.16 g), hydroxylamine hydrochloride (0.84 g) and potassium carbonate (1.82 g) in pyridine (20 ml) was stirred at 80° C. for 3 hours. The reaction mixture was cooled and the solvent was evaporated. The residue was taken up in water and extracted 3 times with $CH_2Cl_2$. The separated organic layer was dried ($MgSO_4$), filtered and the solvent was evaporated. The residue was purified by column chromatography over silica gel (eluent: $CH_2Cl_2$/$CH_3OH$ 95/5). The pure fractions were collected and the solvent was evaporated. The residue was crystallized from $CH_3CN$. The precipitate was filtered off and dried, yielding 1.4 g (42.3%) of 1-[2-[3-(cyclopentyloxy)-4-methoxyphenyl]-2-(hydroxyimino)ethyl]-1,3-dihydro-2H-imidazolone (comp. 3; mp. 191.4° C.).

d) Sodium hydride (1.32 g) was added to dimethylsulfoxide (100 ml) at RT under $N_2$ atmosphere. The reaction mixture was heated up to 60° C. and was stirred for 1 hour. The reaction mixture was cooled to RT and methyltriphenylphosphonium bromide (11.7 g) was added portionwise. The reaction mixture was stirred for 30 minutes. Then compound 1 (3.16 g) was added portionwise. The reaction mixture was stirred for 1 hour, poured out into ice water and extracted three times with diethyl ether (150 ml). The separated organic layer was dried ($MgSO_4$), filtered and the solvent was evaporated. The residue was purified by column chromatography over silica gel (eluent: ethylacetate/ ($CH_3OH/NH_3$) 97.5/2.5). The pure fractions were collected and the solvent was evaporated. The residue was triturated in diethyl ether. The precipitate was filtered off, washed with diethyl ether, then dried, yielding 1 g (32%) of 1-[2-[3-(cyclopentyloxy)-4-methoxy-phenyl]-2-propenyl]-1,3-dihydro-2H-imidazol-2-one (comp. 4; mp. 110.1° C.).

EXAMPLE B.2 a) 1-[2-(3,4-dimethoxyphenyl)-2-oxoethyl]-1,3-dihydro-3-(phenylmethyl)-2H-imidazol-2-one was prepared in a similar way as compound 1, but butyllithium (2.5M in hexane) was used instead of sodium bis(trimethylsilyl) amide (comp. 5; mp. 128.8° C.).

b) Phenyllithium (15 ml) was added to a solution of compound 5 (3.52 g) in THF (100 ml), stirred at −78° C. under a $N_2$ flow. The reaction mixture was stirred for another 2 hours at −78° C. The mixture was allowed to warm to RT, while stirring for one hour. Water (50 ml) was carefully added and the mixture was stirred for 20 minutes, then extracted twice with $CH_2Cl_2$ (100 ml). The separated organic layer was dried (MgSO$_4$), filtered, and the solvent was evaporated. The residue was crystallized from ethanol and the precipitate was filtered off, washed with ethanol and diethyl ether, then dried, yielding 1.27 g of 1-[2-(3,4-dimethoxy-phenyl)-2-oxoethyl]-1,3-dihydro-2H-imidazol-2-one (comp. 6).

EXAMPLE B.3 a) A mixture of ethyl 3-[2-(3,4-dimethoxyphenyl)-2-oxoethyl]-2-oxo-1-imidazolidine-1-carboxylate (0.5 g),prepared according to the procedure described in example B.1.b, and potassium carbonate (14 g) in ethanol (100 ml) was stirred and refluxed for 30 minutes. The reaction mixture was cooled, poured out into water (200 ml) and the resulting mixture was extracted three times with CH$_2$Cl$_2$. The combined organic layers were evaporated and the residue was purified by column chromatography over silica gel (eluent: CH$_2$Cl$_2$/CH$_3$OH 95/5). The pure fractions were collected and the solvent was evaporated. The residue was crystallized from CH$_3$CN and the precipitate was filtered off and dried, yielding 1.8 g (41.7%) of 1-[2-(3,4-dimethoxyphenyl)-2-oxoethyl]-2-imidazolidinone (comp. 7; mp. 166.6° C.).

b) A mixture of compound 7 (2.64 g), 2,3-dihydro-4H-pyran (0.84 g) and p-toluenesulfonic acid monohydrate (cat. quant.) in toluene (50 ml) was stirred at RT for 1 hour. The reaction mixture was stirred and refluxed for another hour. The solvent was evaporated and the residue was purified by short column chromatography over silica gel (eluent: CH$_2$Cl$_2$/CH$_3$OH 98/2). The pure fractions were collected and the solvent was evaporated. The residue was crystallized from ethylacetate and the precipitate was filtered off, washed with ethylacetate and dried, yielding 0.2 g (6%) of (±)-1-[2-(3,4-dimethoxyphenyl)-2-oxoethyl]-3-(tetrahydro-2H-pyran-2-yl)-2-imidazolidinone (comp. 8; mp. 119.7° C.).

c) A mixture of sodium hydride (8.64 g) in THF (700 ml) was stirred at RT under a N$_2$ flow. Diethyl cyanomethylphosphonate (31.86 g) was added dropwise while keeping the temperature below 15° C. The reaction mixture was stirred for 15 minutes. Compound 7 (15.84 g) was added portionwise and stirring was continued for 2 hours. The reaction mixture was cooled on an ice-bath, decomposed with an aqueous NH$_4$Cl solution and this mixture was extracted three times with CH$_2$Cl$_2$. The separated organic layer was dried (MgSO$_4$), filtered, and the solvent was evaporated. The residue was purified by column chromatography over silica gel (eluent: ethylacetate/C$_2$H$_5$OH 99/1). The desired fraction was collected and the solvent was evaporated, the residue was stirred in diisopropyl ether. The precipitate was filtered off and dried, yielding 10.16 g (59%) of (E)-3-(3,4-dimethoxyphenyl)-4-(2-oxo-1-imidazolidinyl)-2-butenenitrile (comp. 9).

EXAMPLE B.4

Sodium hydride (0.2 g; 60%) was added to a cold (0° C.) solution of dimethylformamide (30 ml). A solution of intermediate 4 (1.02 g) in dimethyllformamide (20 ml) was added dropwise and the mixture was stirred for 2 hours under N$_2$ flow. 2-Bromo-1-[3-(cyclopentyloxy)-4-methoxyphenyl]ethanone (1.75 g) was added portionwise and the resulting reaction mixture was stirred for 2 hours. The mixture was cooled to 0° C. A saturated aqueous NH$_4$Cl solution (100 ml) was added dropwise. This mixture was extracted twice with toluene (100 ml). The separated organic layer was dried (MgSO$_4$), filtered and the solvent evaporated. The residue was purified by column chromatography over silica gel (eluent: ethylacetate/(CH$_3$OH/NH$_3$) 97.5/2.5). The desired fractions were collected and the solvent was evaporated. The residue was triturated in DIPE, filtered off, washed with DIPE, then dried, yielding 0.4 g (16%) of 1-[2-[3-(cyclopentyloxy)-4-methoxyphenyl]-2-oxoethyl]-1,3-dihydro-3-[(4-methoxyphenyl)methyl]-2H-imidazol-2-one (comp. 10; mp. 105.5° C.).

EXAMPLE B.5

A mixture of oxalyl chloride (1.91 g) in CH$_2$Cl$_2$ (30 ml) was stirred at −60° C. under N$_2$ flow. A mixture of dimethylsulfoxide (2.36 g) in CH$_2$Cl$_2$ (8 ml) was added dropwise at −60° C. The mixture was stirred at −60° C. for 5 minutes. A mixture of intermediate 6 (3.04 g) in CH$_2$Cl$_2$ (50 ml) was added at −60° C. The mixture was stirred at −60° C. for 15 min. Triethylamine (5.5 g) was added at −60° C. The mixture was stirred at −60° C. for 5 minutes, then allowed to warm to room temperature, decomposed with water (60 ml) and separated into its layers. The aqueous layer was extracted three times with CH$_2$Cl$_2$. The combined organic layer was dried (MgSO$_4$), filtered and the solvent was evaporated. The residue was purified by column chromatography over silica gel (eluent: CH$_2$Cl$_2$/CH$_3$OH 95/5). The pure fractions were collected and the solvent was evaporated. The residue was crystallized from CH$_3$CN, yielding 1.2 g (39.7%) of 1-[2-[3-(cyclopropylmethyloxy)-4-methoxyphenyl]-2-oxoethyl]-1,3-dihydro-2H-imidazol-2-one (comp. 18).

The following compounds were prepared according to one of the above examples (Ex. No.).

TABLE 1

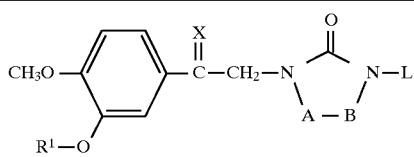

| Comp No | Ex No | R$^1$ | X | —A—B— | L | Physical data |
|---|---|---|---|---|---|---|
| 1 | B.1.a | cyclopentyl | O | —CH=CH— | H | — |
| 2 | B.1.b | cyclopentyl | O | —CH=CH— | C(=O)OC$_2$H$_5$ | mp. 81.3° C. |
| 3 | B.1.c | cyclopentyl | N—OH | —CH=CH— | H | mp. 191.4° C. |
| 4 | B.1.d | cyclopentyl | CH$_2$ | —CH=CH— | H | mp. 110.1° C. |
| 5 | B.2.a | CH$_3$ | O | —CH=CH— | benzyl | mp. 128.8° C. |
| 6 | B.2.b | CH$_3$ | O | —CH=CH— | H | — |
| 7 | B.3.a | CH$_3$ | O | —CH$_2$—CH$_2$— | H | mp. 166.6° C. |
| 8 | B.3.b | CH$_3$ | O | —CH$_2$—CH$_2$— | 2-tetrahydropyranyl | mp. 166.6° C. |

TABLE 1-continued $$CH_3O-\underset{R^1-O}{\underset{|}{\bigcirc}}-\overset{X}{\underset{\|}{C}}-CH_2-N\underset{A-B}{\overset{O}{\underset{\|}{\bigcirc}}}N-L$$

| Comp No | Ex No | $R^1$ | X | —A—B— | L | Physical data |
|---|---|---|---|---|---|---|
| 9 | B.3.c | $CH_3$ | CHCN | $-CH_2-CH_2-$ | H | E isomer |
| 10 | B.4 | cyclopentyl | O | $-CH=CH-$ | 4-methoxybenzyl | mp. 105.5° C. |
| 11 | B.1.a | $CH_3$ | O | $-CH=CH-$ | diphenylmethyl | mp. 140.8° C. |
| 12 | B.1.a | $CH_3$ | O | $-CH=CH-$ | 2,4-dimethoxybenzyl | mp. 129.2° C. |
| 13 | B.3.a | cyclopentyl | O | $-CH_2-CH_2-$ | H | mp. 174.8° C. |
| 14 | B.1.a | cyclopentyl | O | $-CH_2-CH_2-$ | $C(=O)OC_2H_5$ | mp. 97.4° C. |
| 15 | B.1.a | $CH_3$ | O | $-CH_2-CH_2-$ | $C(=O)OC_2H_5$ | mp. 133.9° C. |
| 16 | B.1.a | $CH_3$ | O | $-CH=CH-$ | $C(=O)OC_2H_5$ | mp. 125.5° C. |
| 17 | B.1.c | $CH_3$ | N—OH | $-CH_2-CH_2-$ | H | mp. 171.2° C. |
| 18 | B.5 | cyclopropyl-methyl | O | $-CH=CH-$ | H | — |

C. PHARMACOLOGICAL EXAMPLE

EXAMPLE C.1

Inhibition of Recombinant Human Mononuclear Lymphocyte (MNL) Phosphodiesterase Type IV B Produced in Insect Cells with a Baculovirus Vector The alleviating and/or curing effect of the instant compounds on allergic and atopic diseases was assessed by an in vitro assay system to detect an inhibiting effect on the recombinant human MNL phosphodiesterase type IV B.

Seventy-two hours after infection with recombinant baculovirus, the insect cells were harvested and pelleted at 500 g for 5 minutes. The cells were lysed in 10 ml lysis-buffer consisting of 20 mM Tris, 10 mM EGTA, 2 mM $Na_2EDTA$, 1% Triton-X-100, 1 mM $Na_3VO_4$, 10 mM NaF, 2 µg/ml of leupeptine, pepstatine and aprotinine, 0.3 µg/ml benzamidine and 100 µg/ml TPCK pH 7.5. After 5 minutes on ice, solubilized cells were centrifuged at 4000 rpm for 15 minutes at 4° C. The resulting supernatant was filtered through a 0.45 µm filter (Millipore) and brought to TBS buffer (50 mM Tris, 150 mM NaCl pH 7.4).

The supernatant containing phosphodiesterase (PDE) type IV B, was subsequently loaded onto a 5 ml anti-FLAG-$M_2$ affinity gel column, previously activated with 5 ml 100 mM glycine pH 3.5 and equilibrated with 20 ml 50 mM Tris, 150 mM NaCl pH 7.4. After washing the column with equilibration buffer, PDE IV was eluted in 1.5 ml fractions containing 37.5 µl 1M Tris pH 8. The fractions were dialyzed overnight against 20 mM Tris, 2mM $Na_2EDTA$ and 400 mM NaCl pH 7.5 and tested for PDE IV activity. Indentification was done on SDS PAGE and Western Blot (anti-FLAG-$M_2$). Active fractions were pooled, brought to 10% glycerol and stored at −70° C.

The incubation mixture (pH 8) (200 µl) contained 20 mM Tris, 10 mM magnesium sulphate, 0.8 µM $^3$H-cAMP (310 mCi/mmole) and the phosphodiesterase type IV, the amount depending on the enzymatic activity. A protein concentration was chosen that showed a linear increase of phosphodiesterase activity during an incubation period of maximum 10 minutes at 37° C. and where less than 10% of the initial substrate was hydrolyzed.

When the effect of different compounds on phosphodiesterase activity was tested, the medium without cAMP was incubated with the compound(s) or its carrier (DMSO-1% final concentration) for 5 min. The enzymatic reaction was started by addition of $^3$H-cAMP and stopped 10 min later after transferring the microtiter-plate in a waterbath at 100° C. for 5 min. After cooling to room temperature, alkaline phosphatase (0.25 µg/ml) was added and the mixture was incubated at 37° C. for 20 min. 100 µl of the mixture was subsequently applied to a GF-B filter-microtiter-plate (Millipore) filled with 300 µl DEAE-Sephadex-A25 suspension. The plate was washed 3 times with 75 µl 20 mM Tris pH 7.5 and the filtrates were collected for counting in the Packard Top Count scintillation counter.

The inhibiting effect of the present compounds on recombinant human MNL phosphodiesterase PDE IV B was measured at different concentrations of the instant compounds. The $IC_{50}$ values (expressed in M) were calculated graphically from the thus obtained inhibition values. Compound Nos. 1 and 4 had an $IC_{50}$ value lower than $1 \times 10^{-6}$M. The other compounds had an $IC_{50}$ value higher than or equal to $1 \times 10^{-6}$M.

EXAMPLE C.2

Dextran-Induced Oedema Formation in Mouse Ear

Systemic injection of dextran T500 in normal, non-sensitized mice elicits increased vascular permeability, leading to extravasation and oedema of the extremities. When dextran is injected together with a blue dye, blueing of the ears is the most prominent feature of oedematous response.

Male Swiss mice weighing 24–26 g were orally pretreated with the test compound dissolved in PEG-200 at different concentrations or solvent. One hour later, the mice were given an intravenous injection with an isotonic saline solution containing 12 mg/ml dextran T500 and 2.6 mg/ml pontamine sky-blue dye, in a volume of 0.1 ml per 10 g body weight. One hour and forty-five minutes later, the animals are sacrificed by ether and their ears removed. Extraction and quantification of the extravasated dye is done as described by Van Wauwe and Goossens (Drug Dev. Res. 1986, 8, 213–218).

The extravasation of the dye is characterized by the blueing value which is defined as the concentration of the extracted dye in both ears. The background blueing value was determined once as the mean blueing value obtained by injecting a group of mice with a saline solution containing only dextran T500 and the blue dye. Table 2 lists the percentage inhibition of the extravasation of the dye when compared with the background extravasation of the dye when the test compound was administered at a dose of 5 mg/kg.

TABLE 2

| Comp. No. | % inhibition |
|---|---|
| 1 | 48.3 |
| 2 | 55.6 |
| 5 | 28.7 |
| 7 | 22.6 |
| 8 | 5.2 |
| 9 | 53.8 |
| 10 | 56.0 |
| 11 | 34.6 |
| 12 | 26.4 |
| 13 | 27.9 |
| 15 | 19.2 |

D. COMPOSITION EXAMPLES

The following formulations exemplify typical pharmaceutical compositions suitable for systemic or topical administration to animal and human subjects in accordance with the present invention.

"Active ingredient" (A.I.) as used throughout these examples relates to a compound of formula (I) or a pharmaceutically acceptable addition salt thereof.

EXAMPLE D.1

Film-Coated Tablets
Preparation of Tablet Core

A mixture of 100 g of the A.I., 570 g lactose and 200 g starch was mixed well and thereafter humidified with a solution of 5 g sodium dodecyl sulfate and 10 g polyvinylpyrrolidone in about 200 ml of water. The wet powder mixture was sieved, dried and sieved again. Then there was added 100 g microcrystalline cellulose and 15 g hydrogenated vegetable oil. The whole was mixed well and compressed into tablets, giving 10.000 tablets, each comprising 10 mg of the active ingredient.
Coating To a solution of 10 g methyl cellulose in 75 ml of denaturated ethanol there was added a solution of 5 g of ethyl cellulose in 150 ml of dichloromethane. Then there were added 75 ml of dichloromethane and 2.5 ml 1,2,3-propanetriol. 10 g of polyethylene glycol was molten and dissolved in 75 ml of dichloromethane. The latter solution was added to the former and then there were added 2.5 g of magnesium octadecanoate, 5 g of polyvinylpyrrolidone and 30 ml of concentrated color suspension and the whole was homogenated. The tablet cores were coated with the thus obtained mixture in a coating apparatus.

EXAMPLE D.2

2% Cream 75 mg stearyl alcohol, 2 mg cetyl alcohol, 20 mg sorbitan monostearate and 10 mg isopropyl myristate are introduced into a doublewall jacketed vessel and heated until the mixture has completely molten. This mixture is added to a separately prepared mixture of purified water, 200 mg propylene glycol and 15 mg polysorbate 60 having a temperature of 70° to 75° C. while using a homogenizer for liquids. The resulting emulsion is allowed to cool to below 25° C. while continuously mixing. A solution of 20 mg A.I., 1 mg polysorbate 80 and purified water and a solution of 2 mg sodium sulfite anhydrous in purified water are next added to the emulsion while continuously mixing. The cream, 1 g of the A.I. is homogenized and filled into suitable tubes.

EXAMPLE D.3

2% Topical Gel

To a solution of 200 mg hydroxypropyl β-cyclodextrine in purified water is added 20 mg of A.I. while stirring. Hydrochloric acid is added until complete dissolution and then sodium hydroxide is added until pH 6.0. This solution is added to a dispersion of 10 mg carrageenan PJ in 50 mg propylene glylcol while mixing. While mixing slowly, the mixture is heated to 50° C. and allowed to cool to about 35° C. whereupon 50 mg ethyl alcohol 95% (v/v) is added. The rest of the purified water q.s. ad 1 g is added and the mixture is mixed to homogenous.

EXAMPLE D.4

2% Topical Cream

To a solution of 200 mg hydroxypropyl β-cyclodextrine in purified water is added 20 mg of A.I. while stirring. Hydrochloric acid is added until complete dissolution and next sodium hydroxide is added until pH 6.0. While stirring, 50 mg glycerol and 35 mg polysorbate 60 are added and the mixture is heated to 70° C. The resulting mixture is added to a mixture of 100 mg mineral oil, 20 mg stearyl alcohol, 20 mg cetyl alcohol, 20 mg glycerol monostearate and 15 mg sorbate 60 having a temperature of 70° C. while mixing slowly. After cooling down to below 25° C., the rest of the purified water q.s. ad 1 g is added and the mixture is mixed to homogenous.

EXAMPLE D.5

2% Liposome Formulation

A mixture of 10 g phosphatidyl choline and 1 g cholesterol in 7.5 g ethyl alcohol is stirred and heated at 40° C. until complete dissolution. 2 g A.I. microfine is dissolved in purified water by mixing while heating at 40° C. The alcoholic solution is added slowly to the aqueous solution while homogenizing during 10 minutes. 1.5 g Hydroxypropyl-methylcellulose in purified water is added while mixing until swelling is complete. The resulting solution is adjusted to pH 5.0 with sodium hydroxide 1N and diluted with the rest of the purified water ad 100 g.

We claim:
1. A compound of formula

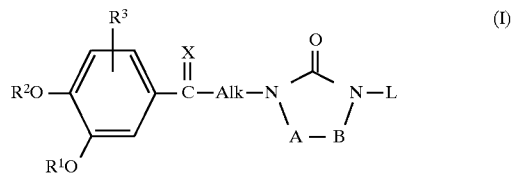

a N-oxide form, a pharmaceutically acceptable acid or base addition salt or a stereochemically isomeric form thereof, wherein:

$R^1$ and $R^2$ each independently are hydrogen; $C_{1-6}$alkyl; difluoromethyl; trifluoromethyl; $C_{3-6}$cycloalkyl; a saturated 5-, 6- or 7-membered heterocycle containing one or two heteroatoms selected from oxygen, sulfur or nitrogen; indanyl; bicyclo[2.2.1]-2-heptenyl; bicyclo[2.2.1]heptanyl; $C_{1-6}$alkylsulfonyl; arylsulfonyl; or $C_{1-10}$alkyl substituted with one or two substituents each independently selected from aryl, pyridinyl, thienyl, furanyl, $C_{3-7}$cycloalkyl and a saturated 5-, 6- or 7-membered heterocycle containing one or two heteroatoms selected from oxygen, sulfur or nitrogen;

$R^3$ is hydrogen, halo or $C_{1-6}$alkyloxy;

is a bivalent radical of formula

 (a-1)

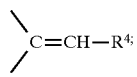 (a-2)

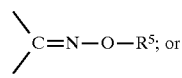 (a-3)

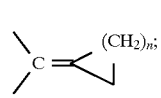 (a-4)

wherein: $R^4$ is hydrogen; cyano: $C_{1-6}$alkyl; $C_{1-4}$alkyloxycarbonyl; $C_{1-6}$alkyl substituted with hydroxy, carboxyl, $C_{1-4}$alkyloxycarbonyl, amino, mono- or di($C_{1-4}$alkyl)amino, $Het^1$ or aryl;

$R^5$ is hydrogen; $C_{1-6}$alkyl; $C_{1-6}$alkyl substituted with hydroxy, carboxyl, $C_{1-4}$alkyloxycarbonyl, amino, aminocarbonyl, mono- or di($C_{1-4}$alkyl)amino, mono- or di($C_{1-4}$alkyl)arninocarbonyl, $Het^1$ or aryl;

n is 1, 2, 3, 4 or 5;

Alk is $C_{1-4}$alkanediyl;

—A—B— is a bivalent radical of formula:

 (b-1)

 (b-2)

wherein each $R^6$ and $R^7$ independently is hydrogen or $C_{1-4}$alkyl;

L is hydrogen; $C_{1-6}$alkyl; $C_{1-6}$alkylcarbonyl; $C_{1-6}$alkyloxycarbonyl; $C_{1-6}$alkyl substituted with one or two substituents selected from the group consisting of hydroxy, $C_{1-4}$alkyloxy, $C_{1-4}$alkyloxycarbonyl, mono- and di($C_{1-4}$alkyl)amino, aryl and $Het^2$; $C_{3-6}$alkenyl; $C_{3-6}$alkenyl substituted with aryl; piperidinyl; piperidinyl substituted with $C_{1-4}$alkyl or aryl$C_{1-4}$alkyl; $C_{1-6}$alkylsulfonyl or arylsulfonyl;

aryl is phenyl or phenyl substituted with one, two or three substituents selected from halo, hydroxy, $C_{1-4}$alkyl, $C_{1-4}$alkyloxy, $C_{3-6}$cycloalkyl, trifluoromethyl, amino, nitro, carboxyl, $C_{1-4}$alkyloxycarbonyl and $C_{1-4}$alkylcarbonylamino;

$Het^1$ is pyridinyl; pyridinyl substituted with $C_{1-4}$alkyl; furanyl; furanyl substituted with $C_{1-4}$alkyl; thienyl; thienyl substituted with $C_{1-4}$alkylcarbonylamino; hydroxypyridinyl, hydroxypyridinyl substituted with $C_{1-4}$alkyl or $C_{1-4}$alkoxy$C_{1-4}$alkyl; imidazolyl; imidazolyl substituted with $C_{1-4}$alkyl; thiazolyl; thiazolyl substituted with $C_{1-4}$alkyl; oxazolyl; oxazolyl substituted with $C_{1-4}$alkyl; isoquinolinyl; isoquinolinyl substituted with $C_{1-4}$alkyl; quinolinonyl, quinolinonyl substituted with $C_{1-4}$alkyl; morpholinyl; piperidinyl; piperidinyl substituted with $C_{1-4}$alkyl, $C_{1-4}$alkyloxycarbonyl or arkyl$C_{1-4}$alkyl; piperazinyl; piperazinyl substituted with $C_{1-4}$alkyl, $C_{1-4}$alkyloxycarbonyl or aryl$C_{1-4}$alkyl; and $Het^2$ is morpholinyl; piperidinyl; piperidinyl substituted with $C_{1-4}$alkyl or arkyl$C_{1-4}$alkyl; piperazinyl; piperazinyl substituted with $C_{1-4}$alkyl or arkyl$C_{1-4}$alkyl; pyridinyl; pyridinyl substituted with $C_{1-4}$alkyl; furanyl; furanyl substituted with $C_{1-4}$alkyl; thienyl or thienyl substituted with $C_{1-4}$alkyl or $C_{1-4}$alkylcarbonylamino.

2. A compound according to claim 1 wherein:

$R^1$ and $R^2$ each independently are hydrogen, $C_{1-6}$alkyl, difluoromethyl, trifluoromethyl, $C_{3-6}$cycloalkyl or bicyclo[2.2.1]-2-heptenyl;

is a bivalent radical of formula

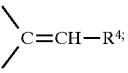 (a-1)

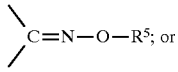 (a-2)

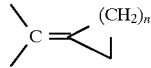 (a-3)

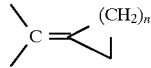 (a-4)

wherein: $R^4$ is hydrogen; $C_{1-6}$alkyl; $C_{1-6}$alkyl substituted with hydroxy, carboxyl, $C_{1-4}$alkyloxycarbonyl, amino, mono- or di($C_{1-4}$alkyl)amino, $Het^1$ or aryl;

$R^5$ is hydrogen; $C_{1-6}$alkyl; $C_{1-6}$alkyl substituted with hydroxy, carboxyl, $C_{1-4}$alkyloxycarbonyl, amino, aminocarbonyl, mono- or di($C_{1-4}$alkyl)amino, mono- or di($C_{1-4}$alkyl)aminocarbonyl, $Het^1$ or aryl;

n is 1, 2, 3, 4 or 5;

L is hydrogen; $C_{1-6}$alkyl; $C_{1-6}$alkyl substituted with hydroxy, $C_{1-4}$alkyloxy, $C_{1-4}$alkyloxycarbonyl, mono- or di($C_{1-4}$alkyl)amino, aryl or $Het^2$; $C_{3-6}$alkenyl; $C_{3-6}$alkenyl substituted with aryl; piperidinyl; piperidinyl substituted with $C_{1-4}$alkyl or aryl$C_{1-4}$alkyl; $C_{1-6}$alkylsulfonyl or arylsulfonyl; aryl is phenyl or phenyl substituted with one, two or three substituents selected from halo, $C_{1-4}$alkyl, $C_{1-4}$alkyloxy, $C_{3-6}$cycloalkyl, trifluoromethyl, amino and $C_{1-4}$alkylcarbonylamino.

3. A compound according to claim 1 wherein

is a radical of formula (a-2), (a-3) or (a-4).

4. A compound according to claim 1 wherein $R^1$ is hydrogen; a saturated 5-, 6- or 7-membered heterocycle containing one or two heteroatoms selected from oxygen, sulfur or nitrogen; bicyclo[2.2.1]-2-heptenyl; $C_{1-6}$alkylsulfonyl; arylsulfonyl; or $C_{1-10}$alkyl substituted with one or two substituents each independently selected from pyridinyl, thienyl, furanyl, $C_{3-7}$cycloalkyl and a saturated 5-, 6- or 7-membered heterocycle containing one or two heteroatoms selected from oxygen, sulfur or nitrogen.

5. A compound according to claim 1 wherein $R^2$ is hydrogen, $C_{3-6}$cycloalkyl; a saturated 5-, 6- or 7-membered heterocycle containing one or two heteroatoms selected from oxygen, sulfur or nitrogen; indanyl; bicyclo[2.2.1]-2-heptenyl; bicyclo[2.2.1]heptanyl; $C_{1-6}$alkylsulfonyl; arylsulfonyl; or $C_{1-10}$alkyl substituted with one or two substituents each independently selected from aryl, pyridinyl, thienyl, furanyl, $C_{3-7}$cycloalkyl and a saturated 5-, 6- or 7-membered heterocycle containing one or two heteroatoms selected from oxygen, sulfur or nitrogen.

6. A compound according to claim 1 or 2 wherein $R^1$ is $C_{1-6}$alkyl or $C_{3-6}$cycloalkyl and $R^2$ is $C_{1-6}$alkyl.

7. A compound according to any one of claims 1 to 6 wherein $R^3$ is hydrogen.

8. A compound according to any one of claims 1 to 7 wherein Alk is methylene or 1,2-ethanediyl.

9. A compound according to any one of claims 1 to 8 wherein L is hydrogen or $C_{1-6}$alkyl.

10. A compound according to any one of claims 1 to 9 wherein —A—B— is a bivalent radical of formula (b-1) wherein $R^6$ and $R^7$ both are hydrogen.

11. A compound according to claim 1 wherein the compound is 1-[2-[3-(cyclopentyloxy)-4-methoxyphenyl]-2-oxoethyl]-1,3-dihydro-2H-imidazol-2-one or 1-[2-[3-(cyclopentyloxy)-4-methoxy-phenyl]-2-propenyl]-1,3-dihydro-2H-imidazol-2-one.

12. A composition comprising a pharmaceutically acceptable carrier and, as active ingredient, a therapeutically effective amount of a compound as claimed in any one of claims 1 to 11.

13. A method of treating asthmatic or atopic diseases in a human in need of such treatment which comprises administering an effective amount of a compound as claimed in any one of claims 1 to 11.

14. A method of treating atopic dermatitis in a human in need of such treatment which comprises administering an effective amount of a compound as claimed in any one of claims 1 to 11.

* * * * *